United States Patent [19]

Ways et al.

[11] Patent Number: 6,103,713
[45] Date of Patent: Aug. 15, 2000

[54] THERAPEUTIC TREATMENT FOR AUTOIMMUNE DISEASES

[75] Inventors: Douglas Kirk Ways, Indianapolis; Daniel Wierda, Greenfield, both of Ind.

[73] Assignee: Eli Lilly and Company, Indianapolis, Ind.

[21] Appl. No.: 09/253,717

[22] Filed: Feb. 22, 1999

Related U.S. Application Data

[60] Provisional application No. 60/076,851, Mar. 5, 1998.

[51] Int. Cl.⁷ .................. A61K 31/33; A61K 31/555; A61K 31/55; A61K 31/415; A61K 31/40
[52] U.S. Cl. .................. 514/183; 514/185; 514/214; 514/397; 514/414; 514/422
[58] Field of Search .................. 514/422, 414, 514/397, 214, 183, 185

[56] References Cited

U.S. PATENT DOCUMENTS

| | | |
|---|---|---|
| 5,057,614 | 10/1991 | Davis et al. . |
| 5,481,003 | 1/1996 | Gillig et al. . |
| 5,491,242 | 2/1996 | Gillig et al. . |
| 5,545,636 | 8/1996 | Heath, Jr. et al. . |
| 5,552,396 | 9/1996 | Heath, Jr. et al. . |
| 5,559,228 | 9/1996 | Gillig et al. . |
| 5,621,098 | 4/1997 | Heath, Jr. et al. . |
| 5,710,145 | 1/1998 | Engel et al. . |
| 5,780,461 | 7/1998 | Heath, Jr. et al. . |

FOREIGN PATENT DOCUMENTS

| | | |
|---|---|---|
| 0 657 411 A1 | 6/1995 | European Pat. Off. . |
| 0 657 458 A1 | 6/1995 | European Pat. Off. . |
| 93 16703 | 9/1993 | WIPO . |
| 93 18173 | 9/1993 | WIPO . |
| 97 40830 | 11/1997 | WIPO . |
| 97 45397 | 12/1997 | WIPO . |
| 98 14186 | 4/1998 | WIPO . |

OTHER PUBLICATIONS

Wilkinson et al. "Isoenzyme specificity of bisindolylmaleimides, selective inhibitors of protein kinase C" Biochem J. (1993) 294 PP. 335–337.

Wilkinson & Nixon "PKC Inhibitors in the Therapy of Autoimmune Diseases" Current Pharmaceutical Design, 2, pp. 596–609 (1996).

J.M. Pfeilschifter: "Regulatory functions of protein kinase C isoenzymes in glomerular mesangial cells" Nephrol Dial Transplant, vol. 9, No. 8, 1994, pp. 1061–1062.

Lisardo Bosca et al.: "B cell triggering by bacterial lipopetide involves both translocation and activation of the membrane–bound form of protein kinase C" J. Immunol., vol. 147, No. 5, 1991, pp. 1463–1469.

Peter D. Davies: "Inhibitors of protein kinase C. 2. Substituted bisindolylmaleimides with improved potency and selectivity" J. Med. Chem., vol. 35, No. 6, 1992, pp. 994–1001.

J.S. Nixon et al.: "Novel, potent and selective inhibitors of protein kinase C show oral anti–inflammatory activity" Drugs Exp Clin Res, vol. 17, No. 8, 1991, pp. 389–393.

*Primary Examiner*—Raymond Henley, III
*Attorney, Agent, or Firm*—Paul R. Darkes

[57] ABSTRACT

Methods for inhibiting activation and/or proliferation of T cells and B cells and for treating autoimmune diseases and/or disease manifestations are disclosed, particularly using the isozyme selective PKC inhibitor, (S)-3,4-[N, N'-1, 1'-((2"-ethoxy)-3'"(O)-4'"-(N,N-dimethylamino)-butane)-bis-(3,3'-indoly 1)]-1(H)-pyrrole-2,5-dione and its pharmaceutically acceptable salts.

20 Claims, No Drawings

THERAPEUTIC TREATMENT FOR AUTOIMMUNE DISEASES

This application claims the benefit of co-pending provisional application Ser. No. 60/076,851 filed Mar. 5, 1998, which is incorporated by reference herein.

BACKGROUND OF THE INVENTION

1. Field of the Invention

The present invention is broadly directed to methods for inhibiting T cell or B cell activation, proliferation, and differentiation, especially activation, proliferation, and differentiation events associated with autoimmune diseases, and for inhibiting production of autoimmune antibodies. The present invention is particularly directed to the use of a particular class of isozyme selective Protein Kinase C (PKC) inhibitors for treating autoimmune diseases and disorders accompanied by undesired T cell or B cell reactivity.

2. Description of Related Art

The development of immunologic responsiveness to self is called autoimmunity and reflects the impairment of self-tolerance. Immunologic, environmental, and genetic factors are closely interrelated in the pathogenesis of autoimmunity. The frequency of autoimmune antibodies (autoantibodies) in the general population increases with age, suggesting a breakdown of self-tolerance with aging. Autoimmune antibodies (autoantibodies) also may develop as an aftermath of tissue damage. The spectrum of autoimmune disorders ranges from thyroiditis, which is organ specific, to systemic lupus erythematosus, which is characterized by an array of autoimmune antibodies (autoantibodies) to cell and tissue antigens.

The development of autoimmunity usually involves the breakdown or circumvention of self-tolerance. The potential for the development of autoimmune antibodies (autoantibodies) probably exists in most individuals. For example, normal human B cells are capable of reacting with several self-antigens, e.g., thyroglobulin, but are suppressed from producing autoimmune antibodies (autoantibodies) by one or more tolerance mechanisms. Precommitted B cells in tolerant individuals can be stimulated in several ways. For example, tolerance involving only T cells, induced by persistent low levels of circulating self-antigens, may breakdown in the presence of substances such as endotoxin. Such substances stimulate the B cells directly to produce autoimmune antibodies (autoantibodies). Another tolerance mechanism involves suppressor T cells. A decrease in suppressor T cell activity therefore may also lead to production of autoimmune antibodies (autoantibodies).

Studies have shown that mouse B-1 B lymphocytes produce many of IgM autoimmune and anti-idiotype antibodies such as cold hemagglutinins, cytosketelal antibodies, and rheumatoid factor (Hayakawa et al., 1984, *Proc. Natl. Acad. Sci. U.S.A.* 81:2494; Herzenberg et al., 198, *Immunological. Rev.* 93:81). It has been demonstrated that overexpression of B-1 B lymphocytes in preclinical models such as the New Zealand Black (NZB) and motheaten viable mice strains is associated with autoimmune diseases (Hayakawa et al., 1983, *J. Exp. Med.* 161:1554; Herzenberg et al., 1986, *Immunological. Rev.* 93:81). Human B cells corresponding to the mouse B-1 B lymphocyte have also been implicated in the production of a variety of human autoimmune antibodies (Plater-Zyberk et al., 1985. *Arth. Rheum.* 28: 971). Thus, overexpression or activation of B-1 B lymphocyte-like cells is associated with disease states related to overproduction of IgM and certain autoimmune disorders.

Cross linking the B cell receptor leads to activation of phospholipase C and production of diacylglycerol. Diacylglycerol induced activation of the conventional and novel members of the PKC gene family is suspected to be involved in mediating certain B cell responses (Baixeras et al., 1993, *Immunol. Rev.* 132:5). Targeted disruption of one member of the PKC gene family, the $\beta$ isoform, produces an immunologically distinct phenotype (Leitges et al., 1996, *Science* 273:788). Transgenic mice lacking the gene for producing PKC-$\beta$ demonstrate reductions in B-1 B lymphocyte number, IgM and IgG3 serum levels, a reduction in immunoglobulin production in response to T cell independent antigen challenge, and a blunted primary response to T cell dependent antigen challenge (Leitges et al., 1996). Thus, protein kinase C-$\beta$ is implicated in modulating B-1 B lymphocyte function and IgM/IgG3 production.

In another preclinical model, PKC-$\beta$ was selectively overexpressed in T lymphocytes using a lck promoter (Snyder & Finn , 1997, *J. Allergy Clin. Immunol.* 99:S307). Transgenic animals carrying the PKC-$\beta$ gene under the control of the distal lck promoter developed a lymphoproliferative disease that became more severe with aging. This result suggests that PKC-$\beta$ may be involved in T cell activation and proliferation as well.

Presently available treatments for autoimmune diseases and disorders are scarce and not completely effective. There remains a need in the art to develop more ways to treat autoimmune diseases.

SUMMARY OF INVENTION

It is an object of the invention to provide a method for inhibiting B cell activation associated with an autoimmune disease.

It is another object of the invention to provide a method for inhibiting B cell proliferation associated with an autoimmune disease.

It is yet another object of the invention to provide a method for inhibiting production of autoimmune antibodies.

It is another object of the invention to provide a method for inhibiting T cell activation associated with an autoimmune disease and for treating an autoimmune disease associated with T cell activation.

It is yet another object of the invention to provide a method for inhibiting T cell proliferation associated with an autoimmune disease and for treating an autoimmune disease associated with T cell proliferation.

It is still another object of the invention to provide a method for treating an autoimmune disease associated with B cell activation.

It is still yet another object of the invention to provide a method for treating an autoimmune disease associated with overproduction of immunoglobulins.

These and other objects of the invention are provided by one or more of the embodiments provided below.

In one embodiment of the invention there is provided a method for inhibiting B cell activation and proliferation which comprises administering to a mammal in need of such treatment a therapeutically effective amount of a particular class of protein kinase C inhibitors.

In another embodiment of the invention there is provided a method for inhibiting production of autoimmune antibodies which comprises administering to a mammal in need of such treatment a therapeutically effective amount of a particular class of protein kinase C inhibitors.

In yet another embodiment of the invention there is provided a method for inhibiting T cell activation and proliferation associated with an autoimmune disease which comprises administering to a mammal in need of such treatment a therapeutically effective amount of the protein kinase C inhibitor.

In still another embodiment of the invention there is provided a method for treating an autoimmune disease associated with B cell activation, overproduction of immunoglobulins, T cell activation or T cell proliferation which comprises administering to a mammal in need of such treatment a therapeutically effective amount of the protein kinase C inhibitor.

The present invention identifies compounds which are effective in treating autoimmune diseases and disorders, especially those associated with B cell activation and/or overproduction of immunoglobulins.

DETAILED DESCRIPTION OF THE INVENTION

It is a discovery of the present invention that the therapeutic use of a particular class of protein kinase C inhibitors, i.e., inhibitors of the β isozyme of protein kinase C, and especially β isozyme selective inhibitors of PKC, inhibits activation, proliferation, and/or differentiation of B cells and T cells, and especially such activation and proliferation events associated with autoimmune diseases, and also inhibits production of autoimmune antibodies (autoantibodies). Consequently, such compounds can be used therapeutically to treat autoimmune diseases and disorders.

The method of this invention preferably utilizes those protein kinase C inhibitors that effectively inhibit the β isozyme. One suitable group of compounds are generally described in the prior art as bis-indolylmaleimides or macrocyclic bis-indolylmaleimides. Bis-indolylmaleimides well recognized in the prior art include those compounds described in U.S. Pat. Nos. 5,621,098, 5,552,396, 5,545,636, 5,481,003, 5,491,242, and U.S. Pat. No. 5,057,614, all incorporated by reference herein. Macrocyclic bis-indolylmaleimides are particularly represented by the compounds of formula I. These compounds, and methods for their preparation, have been disclosed in U.S. Pat. No. 5,552,396, which is incorporated herein by reference.

These compounds are administered in a therapeutically effective amount to a mammal, e.g., a human, to inhibit activation and/or proliferation of B cells and T cells, to inhibit productions of autoimmune antibodies, and to treat autoimmune diseases or disorders, especially those associated with B cell or T cell activation. These compounds can also be administered to patients at risk of the disease conditions mentioned above as prophylactics. Furthermore, these compounds can also be used as immunosuppressors to treat tissue and organ rejections, e.g., acute rejection in organ transplantation.

One preferred class of compounds for use in the method of the invention has the following formula (I):

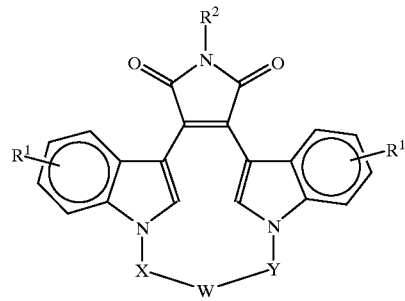

wherein:

W is —O—, —S—, —SO—, —SO$_2$—, —CO—, C$_2$-C$_6$ alkylene, substituted alkylene, C$_2$-C$_6$ alkenylene, -aryl-, -aryl(CH$_2$)$_m$O—, -heterocycle-, -heterocycle—(CH) O—$_{,2}$-fused bicyclic-, -fused bicyclic—(CH$_2$)$_m$ O—, —NR$^3$—, —NOR$^3$—, —CONH—, or —NHCO—;

X and Y are independently C$_1$-C$_4$ alkylene, substituted alkylene, or together X, Y, and W combine to form —(CH$_2$)$_n$—AA—;

R$^1$s are hydrogen or up to four optional substituents independently selected
  from halo, C$_1$-C$_4$ alkyl, hydroxy, C$_1$-C$_4$ alkoxy, haloalkyl, nitro, —NR$^4$R$^5$, or —NHCO(C$_1$-C$_4$ alkyl);

R$^2$ is hydrogen, CH$_3$CO—, —NH$_2$, or hydroxy;

R$^3$ is hydrogen, —(CH$_2$)$_m$aryl, -C$_1$-C$_4$ alkyl, —COO (C$_1$-C$_4$ alkyl), —CONR$^4$R$^5$, —(C=NH)NH$_2$, —SO (C$_1$-C$_4$ alkyl), —SO$_2$ (NR$^4$R$^5$), or —SO$_2$ (C$_1$-C$_4$ alkyl);

R$^4$ and R$^5$ are independently hydrogen, C$_1$-C$_4$ alkyl, phenyl, benzyl, or combine with the nitrogen to which they are bonded to form a saturated or unsaturated 5 or 6 member ring;

AA is an amino acid residue;

m is independently 0, 1, 2, or 3; and n is independently 2, 3, 4, or 5, or a pharmaceutically acceptable salt, prodrug or ester thereof.

A more preferred class of compounds for use in this invention is represented by formula I wherein the moieties —X—W—Y— contain 4 to 8 atoms, which may be substituted or unsubstituted. Most preferably, the moieties —X—W—Y— contain 6 atoms.

Other preferred compounds for use in the method of this invention are those compounds of formula I wherein R$^1$ and R$^2$ are hydrogen; and W is a substituted alkylene, —O—, S—, —CONH—, —NHCO— or —NR$^3$—. Particularly preferred compounds for use in the invention are compounds of the formula Ia:

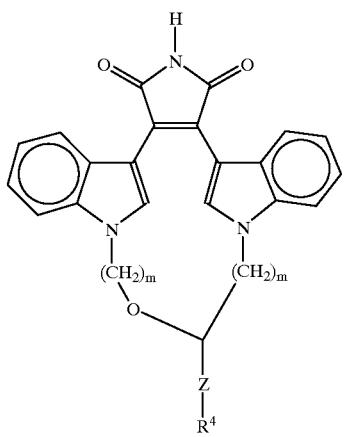

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$) (CF$_3$), —NH(CF$_3$), or —NR$^5$R$^6$; R$^5$ is hydrogen or C$_1$–C$_4$ alkyl; R$^6$ is hydrogen, C$_1$–C$_4$ alkyl or benzyl; p is 0, 1, or 2; and m is independently 2 or 3, or a pharmaceutically acceptable salt, prodrug or ester thereof. Most preferred compounds of the formula Ia are those wherein Z is CH$_2$; and R$^4$ is —NH$_2$, —NH(CF$_3$), or —N(CH$_3$)$_2$, or a pharmaceutically acceptable salt, prodrug or ester thereof.

Other preferred compounds for use in the method of the present invention are compounds wherein W in formula I is —O—, Y is a substituted alkylene, and X is an alkylene. These preferred compounds are represented by formula Ib:

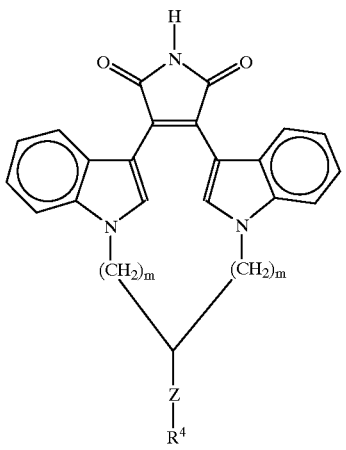

(Ib)

wherein Z is —(CH$_2$)$_p$—; R$^4$ is —NR$^5$R$^6$, —NH(CF$_3$), or —N(CH$_3$) (CF$_3$); R$^5$ and R$^6$ are independently H or C$_1$–C$_4$ alkyl; p is 0, 1, or 2; and m is independently 2 or 3, or a pharmaceutically acceptable salt, prodrug or ester thereof. Most preferred compounds of formula Ib are those wherein p is 1; and R$^5$ and R$^6$ are methyl.

Because they contain a basic moiety, the compounds of formulae I, Ia, and Ib can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4-dioate, 3-hexyne-2, 5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, βhydroxybutyrate, glycolate, maleate, tartrate, methanesulfonate, propanesulfonate, naphthalene-1-sulfonate, naphthalene-2-sulfonate, mandelate and the like. Particularly the hydrochloric and mesylate salts are used.

In addition to pharmaceutically-acceptable salts, other salts also can exist. They may serve as intermediates in the purification of the compounds, in the preparation of other salts, or in the identification and characterization of the compounds or intermediates.

The pharmaceutically acceptable salts of compounds of formulae I, Ia, and Ib can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent.

It is recognized that various stereoisomeric forms of the compounds of formulae I, Ia, and Ib may exist; for example, W may contain a chiral carbon atom in the substituted alkylene moiety. The compounds are normally prepared as racemates and can conveniently be used as such. Alternatively, both individual enantiomers can be isolated or synthesized by conventional techniques if so desired. Such racemates and individual enantiomers and mixtures thereof form part of the compounds used in the methods of the present invention.

The compounds utilized in this invention also encompass the pharmaceutically acceptable prodrugs of the compounds of formulae I, Ia, and Ib. A prodrug is a drug which has been chemically modified and may be biologically inactive at its site of action, but which may be degraded or modified by one or more enzymatic or other in vivo processes to the parent bioactive form. This prodrug likely may have a different pharmacokinetic profile than the parent, enabling easier absorption across the mucosal epithelium, better salt formation or solubility, and/or improved systemic stability (an increase in plasma half-life, for example). Typically, such chemical modifications include the following:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in 11. Bundgaard, *Design of Prodrugs*, (1985).

The synthesis of various bis-indole-N-maleimide derivatives is described in Davis et al. U.S. Pat. No. 5,057,614 and the synthesis of the preferred compounds suitable for use in this invention are described in the previously identified U.S. Pat. No. 5,552,396 and in Faul et al. EP publication 0 657 411 A1, all of which are incorporated herein by reference.

One particularly preferred protein kinase C-β inhibitor for use in the method of this invention is the compound described in Example 5 g ((S)-3,4-[N, N'-1,1'-((2"-ethoxy)-3'"(O)-4'"-(N,N-dimethylamino)-butane)-bis-(3,3'-indoly 1)]-1(H)-pyrrole-2,5dione Hydrochloride Salt) of the aforementioned U.S. Pat. No. 5,552,396. This compound is a potent protein kinase C inhibitor. It is selective to protein kinase C over other kinases and is highly isozyme-selective, i.e., it is selective for the beta-1 and beta-2 isozymes. Other salts of this compound also would be favored, especially the mesylate salts, as described in U.S. Pat. No. 5,710,145 (incorporated herein by reference).

A preferred mesylate salt can be prepared by reacting a compound of the formula II:

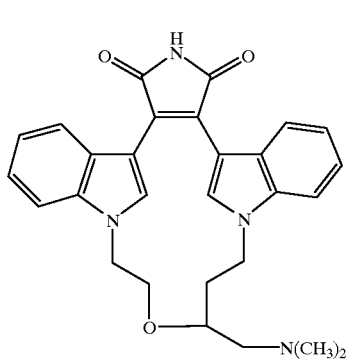

(II)

with methanesulfonic acid in a non-reactive organic solvent, preferably an organic/water mixture, and most preferably water-acetone. Other solvents such as methanol, acetone, ethylacetate and mixtures thereof are operable. The ratio of solvent to water is not critical and generally determined by the solubility of the reagents. Preferred solvent to water ratios are generally from 0.1:1 to 100:1 solvent to water by volume. Preferably, the ratio is 1:1 to 20:1 and most preferably 5:1 to 10:1. The optimal ratio is dependent on the solvent selected and is preferably acetone at a 9:1 solvent to water ratio.

The reaction usually involves approximately equimolar amounts of the two reagents, although other ratios, especially those wherein the methanesulfonic acid is in excess, are operative. The rate of addition of methanesulfonic acid is not critical to the reaction and may be added rapidly (<5 minutes) or slowly over 6 or more hours. The reaction is carried out at temperatures ranging from 0° C. to reflux. The reaction mixture is stirred until formation of the salt is complete, as determined by x-ray powder diffraction and can take from 5 minutes to 12 hours.

The salts of the present invention are preferably and readily prepared as a crystalline form. The trihydrate form of the salt may be readily converted to the monohydrate upon drying or exposure to 20–60% relative humidity. The salt is substantially crystalline demonstrating a defined melting point, birefringence, and an x-ray diffraction pattern. Generally, the crystals have less than 10% amorphous solid and preferably less than 5% and most preferably less than 1% amorphous solid.

The mesylate salt is isolated by filtration, or other separation techniques appreciated in the art, directly from the reaction mixture in yields ranging from 50% to 100%. Recrystallization and other purification techniques known in the art may be used to purify the salt further if desired.

The inhibitors of the β isozyme of PKC described in the present invention can be used to inhibit activation, proliferation, and/or differentiation of B cells and T cells, and to treat autoimmune disorders or clinical manifestations associated therewith.

B cell activation includes activation, redistribution, reorganization, or capping of one or more various B cell membrane receptors, or membrane-bound immunoglobulins. B cells carry membrane-bound immunoglobulins, e.g., IgM, IgG, and IgD, as well as the synthesis or production of antibodies or immunoglobulins. The membrane-bound immunoglobulin molecule is attached by its crystallizable fragment (Fc) portion to the plasma membrane, leaving the antigen-binding sites freely available. Most B cells have membrane receptors for Fc portion of IgG in the form of either antigen-antibody complexes or aggregated IgG. B cells also carry membrane receptors for the activated components of complement, e.g., C3b, C3d, C4, and Clq. These various membrane receptors and membrane-bound immunoglobulins have membrane mobility and can undergo redistribution and capping.

B cell activation also includes the synthesis or production of antibodies or immunoglobulins. Immunoglobulins are synthesized by the B cell series and have common structural features and structural units. Five immunoglobulin classes, i.e., IgG, IgA, IgM, IgD, and IgE, are recognized on the basis of structural differences of their heavy chains including the amino acid sequence and length of the polypeptide chain. Antibodies to a given antigen may be detected in all or several classes of immunoglobulins or may be restricted to a single class or subclass of immunoglobulin. Autoantibodies or autoimmune antibodies may likewise belong to one or several classes of immunoglobulins. For example, rheumatoid factors (antibodies to IgG) are most often recognized as an IgM imnnunoglobulin, but can also consist of IgG or IgA.

In addition, B cell activation also is intended to include a series of events leading to B cell clonal expansion from precursor B lymphocytes and differentiation into antibody-synthesizing plasma cells which takes place in conjunction with antigen-binding and with cytokine signals from other cells.

B cell proliferation includes B cell growth, multiplication, and replication of nucleic acids within B cells, e.g., DNA replication. B cell proliferation could also be considered another form of B cell activation.

Aberrant B cell activation, proliferation, and/or differentiation can lead to enhanced autoimmunity. Several autoimmune diseases are associated with B cell activation, e.g., systemic lupus erythematosus, chronic graft versus host disease, and rheumatoid arthritis. Autoimmune disorders are also associated with B cell activation and/or proliferation, especially overproduction of immunoglobulins, e.g., Waldenstrom's macroglobulinemia, hyperviscosity syndrome, monoclonal gammopathy of undetermined origin, POEMS syndrome, myeloma, macroglobulinemia, and cold agglutinin disease. These disease states are treated by the therapy of the present invention, involving the administration of a therapeutically effective amount of the above-noted PKC inhibitor compounds.

T cells play a key role in cell—mediated immunity. Upon exposure to immunogen, T cells proliferate and differentiate to sensitized lymphocytes that form the basis of cell-mediated immunity. Subsets of T cells function as helper T cells which stimulate B-cell activity, or as suppressor T cells which suppress humoral and cell-mediated immune responses. T cell activation includes sensitization of T cells, T cell production of lymphokines, and interaction of T cells with their effector cells. T cell proliferation includes T cell growth, multiplication of T cells, and replication of nucleic acids within T cells, i.e., DNA replication.

T cell activation also can be associated with autoimmune disorders or disease manifestations, e.g., cryptogenic fibrosing alveolitis, rheumatoid arthritis, reactive arthritis, Reiter's arthritis, systemic lupus eyrthematosis, polymyositis, dermatomyositis, localized scleroderma, cutaneous scleroderma, systemic scleroderma, Sjorgen's syndrome, Raynaud's phenomenon, Bechet's disease, Kawasaki's disease (infantile acute febrile mucocutaneous lymph node syndrome), antiglomerular renal membrane disease, primary biliary sclerosis, primary sclerosing cholangitis, ulcerative colitis, and Crohn's disease. As above, these autoimmune disorders and diseases are treated by administering a therapeutically effective amount of the above-noted PKC inhibitor compounds.

Certain autoimmune disorders display a prominent degree of T cell proliferation in their pathogenesis and disease manifestation, e.g., T cell lymphomas including adult T cell lymphoma, Sezary syndrome, peripheral T cell lymphoma, large cell lymphoma, certain forms of chronic lymphoblastic lymphoma, certain forms of Non Hodgkin's lymphoma, and T cell lymphoproliferative syndrome; T cell leukemias including T cell acute lymphoblastic leukemia, Sezary cell leukemia, large granular leukemia, T cell prolymphocytic leukemia, and adult T cell leukemia especially adult T cell leukemia not associated with human T cell lymphotrophic virus type 1 infection; Hairy cell leukemia including cutaneous T cell neoplasias, Sezary syndrome, and mycosis fungoides; juvenile onset diabetes; and pagetoid reticulosis. As above, these autoimmune disorders and diseases are treated by administering a therapeutically effective amount of the above-noted PKC inhibitor compounds.

One skilled in the art will recognize that a therapeutically effective amount of the protein kinase C inhibitor of the present invention is the amount sufficient to either inhibit the activation and/or proliferation of T cells and B cells associated with autoimmune diseases, or to inhibit the productions of autoimmune antibodies. Such amount varies inter alia, depending upon the concentration of the compound in the therapeutic formulation, the body weight of the patient, the condition of the patient and the method of application.

Generally, an amount of protein kinase C inhibitor to be administered as a therapeutic agent will be determined on a case by case basis by the attending physician. As a guideline, the degree of antibody production, the T cell and B cell counts, the degree of syndromes derived from autoimmune diseases, the duration of the autoimmunity, the association with other diseases, the body weight, and the age of a patient, the mode of administration, and the like will be considered when setting an appropriate dose. Other factors to be considered when getting an appropriate dosage include the patient's genetic heritages.

Generally, a suitable dose is one that results in a concentration of the protein kinase C inhibitor at the treatment site in the range of 0.5 nM to 200 $\mu$M, and more usually between about 0.5 nM to 200 nM. It is expected that serum concentrations of 0.5 nM to 20 nM should be sufficient in many circumstances.

To obtain these treatment concentrations, a patient in need of treatment likely will be administered between about 0.001 mg per day per kg of body weight and 50.0 mg per day per kg. Usually, not more than about 10.0 mg per day per kg of body weight of protein kinase C inhibitor should be needed. As noted above, the above amounts may vary on a case-by-case basis.

The therapeutic effects of the methods in the present invention can be evaluated by examining the effects of the PKC isozyme selective inhibitors on preclinical models of autoimmune diseases and lymphocytes derived from these animals. Specifically, the effects of the compounds of formula I and the preferred compounds of formula Ia and Ib on the disease manifestation, the production of autoimmune antibodies, e.g., IgM, and on T and B cell subsets, e.g., CD3, CD4, $SF_{gm}$, can be examined. For example, a decrease in disease manifestation in autoimmune animal models such as New Zealand Black (NZB), motheaten mice, or collagen induced arthritis is predictive of a positive response in preventing or inhibiting autoimmune diseases.

The effects of the compounds on activation, proliferation, and/or differentiation of T cells and B cells could also be determined in vitro. For example, T cells can be challenged with antigens or mitogens in vitro. T cell activation in response to the antigen or mitogen challenge can be examined in the absence or presence of PKC inhibitors of the present invention. An inhibition of T cell reactivity in vitro is predicative of a positive response in abrogating T cell effector function associated with autoimmune diseases. Similarly, the effect of PKC inhibitors on B lymphocyte function could be tested in vitro by mitogen or antigen stimulation. This includes measuring effects on specific antibody production. An inhibitory effect of the PKC inhibitors is predictive of a positive response in inhibiting B cell responses associated with autoimmune diseases.

The compounds of formula I, and the preferred compounds of formula Ia and Ib are preferably formulated prior to administration. Suitable pharmaceutical formulations are prepared by known procedures using well known and readily available ingredients. In making the compositions suitable for use in the method of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders for either oral or topical application.

Some examples of suitable carriers, excipient, and diluents include lactose, dextrose, sucrose sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 0.05 mg to about 3 g, more usually about 5–15 mg of the active ingredient. However, it will be understood that the therapeutic dosage administered will be determined by the physician in the light of the relevant circumstances including the severity of the condition to be treated, the choice of compound to be administered and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, most of which may be administered orally, the compounds used in the method of the present invention also may be administered topically. Topical formulations include ointments, creams and gels. In a preferred embodiment, intracavernosal injection of the compound directly to the smooth muscle is used.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (compound) customarily is added in an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent.

The amount of compound incorporated into a topical formulation is not critical; the concentration should be within a range sufficient to permit ready application of the formulation to the affected area in an amount which will deliver the desired amount of compound to the desired treatment site.

The customary amount of a topical formulation to be applied to an affected tissue will depend upon concentration of compound in the formulation. Generally, the formulation will be applied to the effected tissue in an amount affording from about 1 to about 500 µg compound per cm$^2$ of an affected tissue. Preferably, the applied amount of compound will range from about 30 to about 300 µg/cm$^2$, more preferably, from about 50 to about 200 µg/cm$^2$, and, most preferably, from about 60 to about 100 µg/cm$^2$.

The following formulation examples are illustrative only and are not intended to limit the scope of the invention in any way.

FORMULATION 1

Hard gelatin capsules are prepared using the following ingredients:

|  | Quantity (mg/capsule) |
| --- | --- |
| Active agent | 5 |
| starch, dried | 200 |
| magnesium stearate | 10 |
| Total | 215 mg |

The above ingredients are mixed and filled into hard gelatin capsules in 460 mg quantities.

FORMULATION 2

A tablet is prepared using the ingredients below:

|  | Quantity (mg/capsule) |
| --- | --- |
| Active agent | 15 |
| cellulose, microcrystalline | 10 |
| silicon dioxide, fumed | 10 |
| stearic acid | 5 |
| Total | 40 mg |

The components are blended and compressed to form tablets each weighing 665 mg.

FORMULATION 3

Tablets each containing 60 mg of active ingredient are made as follows:

|  | Quantity (mg/tablet) |
| --- | --- |
| Active agent | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A method for inhibiting B cell activation or differentiation associated with an autoimmune disease which comprises administering to a mammal in need of such treatment, a therapeutically effective amount of an inhibitor of the β isozyme of protein kinase C.

2. The method of claim 1 wherein the inhibitor of the β isozyme of protein kinase C is a bis-indolylmaleimide or a macrocyclic bis-indolylmaleimide.

3. The method of claim 1 wherein the inhibitor is β-isozyme selective and where the isozyme selectivity is selected from the group consisting of beta-1 and beta-2 isozymes.

4. The method of claim 3 wherein the protein kinase C inhibitor has the following formula:

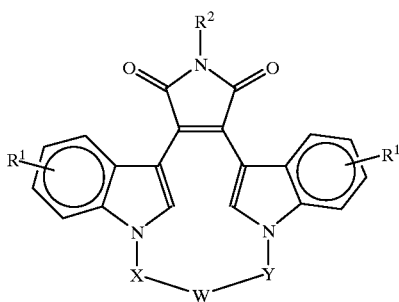

(I)

wherein:

W is —O—, —S—, —SO—, —SO$_2$—, —CO—, $C_2$-$C_6$ alkylene, substituted alkylene, $C_2$-$C_6$ alkenylene, -aryl-, -aryl(CH$_2$)$_m$O—, -heterocycle-, -heterocycle-(CH$_2$)$_m$O—, -fused bicyclic-, -fused bicyclic—(CH$_2$)$_m$O—, —NR$^3$—, —NOR$^3$—, —CONH—, or —NHCO—;

X and Y are independently $C_1$-$C_4$ alkylene, substituted alkylene, or together X, Y, and W combine to form —(CH$_2$)$_n$—AA—;

R$_1$s are hydrogen or up to four optional substituents independently selected from halo, $C_1$-$C_4$ alkyl, hydroxy, $C_1$-$C_4$ alkoxy, haloalkyl, nitro, NR$^4$R$^5$, or —NHCO($C_1$-$C_4$ alkyl);

R$^2$ is hydrogen, CH$_3$CO—, NH$_2$, or hydroxy;

R$^3$ is hydrogen, —(CH$_2$)$_m$aryl, -$C_1$-$C_4$ alkyl, —COO ($C_1$-$C_4$alkyl), —CONR$^4$R$^5$, —(C=NH)NH$_2$,—SO ($C_1$-$C_4$alkyl),—SO$_2$ (NR$^4$R$^5$), or —SO$_2$ ($C_1$-$C_4$alkyl);

R$^4$ and R$^5$ are independently hydrogen, $C_1$-$C_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5 or a pharmaceutically acceptable salt, prodrug or ester thereof.

5. The method of claim 4 wherein the protein kinase C inhibitor has the following formula:

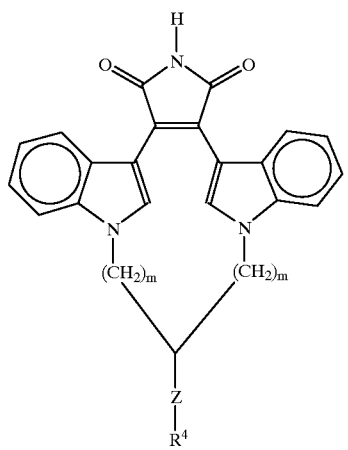

(Ia)

wherein Z is —(CH$_2$)$_p$— or —(CH$_2$)$_p$—O—(CH$_2$)$_p$—; R$^4$ is hydroxy, —SH, $C_1$-$C_4$ alkyl, (CH$_2$)$_m$aryl, —NH(aryl), —N(CH$_3$) (CF$_3$), —NH(CF$_3$), or —NR$^5$R$^6$; R$^5$ is hydrogen or $C_1$-$C_4$ alkyl; R$^6$ is hydrogen, $C_1$-$C_4$ alkyl or benzyl; p is 0, 1, or 2; and m is independently 2 or 3, or a pharmaceutically acceptable salt, prodrug or ester thereof.

6. The method of claim 4 wherein the protein kinase C inhibitor has the following formula:

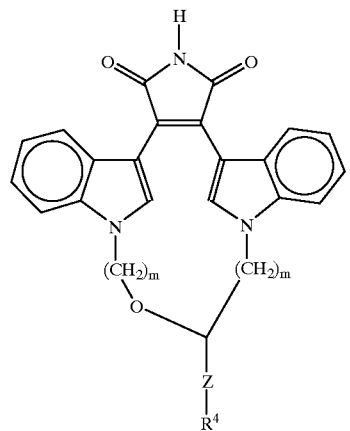

(Ib)

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or $C_1$-$C_4$ alkyl; p is 0, 1, or 2; and m is independently 2 or 3, or a pharmaceutically acceptable salt, prodrug or ester thereof.

7. The method of claim 4, wherein the protein kinase C inhibitor comprises (S)-3,4-[N, N'-1,1 '-((2"-ethoxy)-3'"(O)-4'"-(N,N-dimethylamino)-butane)-bis-(3,3'-indolyl1)]-1(H)-pyrrole-2,5-dione or its pharmaceutically acceptable acid salt.

8. A method for inhibiting B cell proliferation associated with an autoimmune disease which comprises administering to a mammal in need of such treatment, a therapeutically effective amount of an inhibitor of the β isozyme of protein kinase C.

9. A method for inhibiting a production of an autoimmune antibody which comprises administering to a mammal in need of such treatment, a therapeutically effective amount of an inhibitor of the β isozyme of protein kinase C.

10. The method of claim 9 wherein the autoimmune antibody is selected from the group consisting of IgM, IgG, and IgA.

11. A method for inhibiting T cell activation associated with an autoimmune disease which comprises administering to a mammal in need of such treatment, a therapeutically effective amount of an inhibitor of the β isozyme of protein kinase C.

12. A method for inhibiting T cell proliferation associated with an autoimmune disease which comprises administering to a mammal in need of such treatment, a therapeutically effective amount of an inhibitor of the β isozyme of protein kinase C.

13. A method for treating an autoimmune disease associated with B cell activation which comprises administering to a mammal in need of such treatment, a therapeutically effective amount of an inhibitor of the β isozyme of protein kinase C.

14. The method of claim 13 wherein the autoimmune disease is selected from the group consisting of systemic lupus erythematosus, chronic graft versus host disease, Waldenstrom's macroglobulinemia, hyperviscosity syndrome, monoclonal gammopathy of undetermined origin, POEMS syndrome, myeloma, macroglobulinemia, and cold agglutinin disease.

15. A method for treating an autoimmune disease associated with overproduction of immunoglobulins which comprises administering to a mammal in need of such treatment, a therapeutically effective amount of an inhibitor of the β isozyme of protein kinase C.

16. The method of claim 15 wherein the autoimmune disease is selected from the group consisting of Waldenstrom's macroglobulinemia, hyperviscosity syndrome, monoclonal gammopathy of undetermined origin, POEMS syndrome, myeloma, macroglobulinemia, and cold agglutinin disease.

17. A method for treating an autoimmune disease associated with T cell activation which comprises administering to a mammal in need of such treatment, a therapeutically effective amount of an inhibitor of the β isozyme of protein kinase C.

18. The method of claim 17 wherein the autoimmune disease is selected from the group consisting of cryptogenic fibrosing alveolitis, reactive arthritis, Reiter's arthritis, polymyositis, dermatomyositis, localized scleroderma, cutaneous scleroderma, systemic scleroderma, Sjorgen's syndrome, Raynaud's phenomenon, Bechet's disease, Kawasaki's disease, antiglomerular renal membrane disease, primary biliary sclerosis, primary sclerosing cholangitis, ulcerative colitis, and Crohn's disease.

19. A method for treating an autoimmune disease associated with T cell proliferation which comprises administering to a mammal in need of such treatment, a therapeutically effective amount of an inhibitor of the β isozyme of protein kinase C.

20. The method of claim 19 wherein the autoimmune disease is selected from the group consisting of adult T cell lymphoma, Sezary syndrome, peripheral T cell lymphoma, large cell lymphoma, certain forms of chronic lymphoblastic lymphoma, certain forms of Non Hodgkin's lymphoma, T cell lymphoproliferative syndrome, T cell acute lymphoblastic leukemia, Sezary cell leukemia, large granular leukemia, T cell prolymphocytic leukemia, adult T cell leukemia not associated with human T cell lymphotrophic virus type 1 infection, cutaneous T cell neoplasias, mycosis fungoides, juvenile onset diabetes, and pagetoid reticulosis.

* * * * *